Figure 1A:
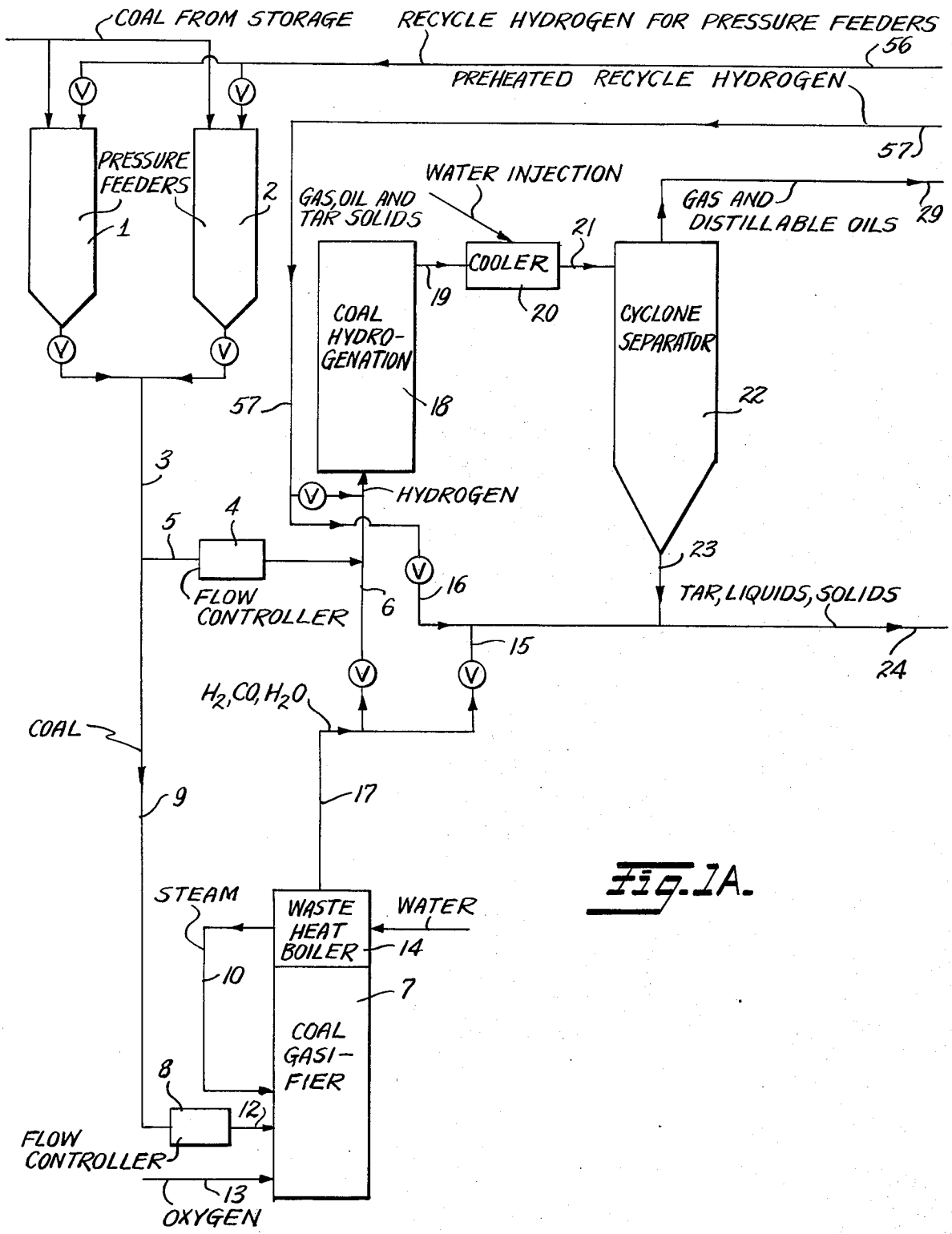

United States Patent [19]
Schroeder

[11] 3,944,480

[45]*Mar. 16, 1976

[54] PRODUCTION OF OIL AND HIGH BTU GAS FROM COAL

[76] Inventor: Wilburn C. Schroeder, 7316 Radcliffe Drive, College Park, Md. 20740

[ * ] Notice: The portion of the term of this patent subsequent to July 9, 1991, has been disclaimed.

[22] Filed: Mar. 29, 1974

[21] Appl. No.: 456,163

[52] U.S. Cl.................. 208/10; 208/8; 48/197 R
[51] Int. Cl.$^2$........................................... C10G 1/06
[58] Field of Search.................. 208/10, 8; 48/197 R

[56] References Cited
UNITED STATES PATENTS

| | | | |
|---|---|---|---|
| 3,030,297 | 4/1962 | Schroeder | 208/8 |
| 3,194,644 | 7/1965 | Gorin et al. | 48/197 R |
| 3,453,202 | 7/1969 | Friedman et al. | 208/10 |
| 3,503,866 | 3/1970 | Skripek et al. | 208/8 |
| 3,708,269 | 1/1973 | Linden | 48/197 R |
| 3,729,407 | 4/1973 | Camp et al. | 208/10 |
| 3,755,137 | 8/1973 | Schuman | 208/10 |
| 3,823,084 | 7/1974 | Schroeder | 208/10 |

*Primary Examiner*—Delbert E. Gantz
*Assistant Examiner*—James W. Hellwege
*Attorney, Agent, or Firm*—Bacon & Thomas

[57] ABSTRACT

Hydrocarbon oils and gases of high Btu content are produced from coal in a pressurized closed cyclic system through which hydrogen is recycled. Coal, oxygen and steam are fed into the pressurized system and oil and high Btu gas are removed as products. The system includes a coal gasification zone and coal and tar hydrogenation zones which receive hydrogen-containing gases from the coal gasification zone along with recycle hydrogen. The product oil is separated from the combined effluent of the hydrogenation zones and the resulting gases are then purified and separated into product hydrocarbon gases and recycle hydrogen without substantial reduction in system pressure.

14 Claims, 3 Drawing Figures

PRODUCTION OF OIL AND HIGH BTU GAS FROM COAL

COPENDING APPLICATIONS

This application is related to my co-pending applications Ser. No. 268,201 filed June 30, 1972 now U.S. Pat. No. 3,823,084 and Ser. No. 412,026 filed Nov. 1, 1973.

The present invention relates to the conversion of coal into liquid and gaseous hydrocarbon products by reacting hydrogen with the chemical substituents of coal in a closed, cyclic, high pressure system through which hydrogen is circulated. The only raw materials fed to the system are coal, oxygen and water. Hydrogen required for the hydrogenation is produced from the coal.

My prior U.S. Pat. Nos. 3,030,297, issued Apr. 17, 1962, and 3,152,063, issued Oct. 6, 1964, disclose coal hydrogenation processes and set forth the general conditions of temperature, pressure and time under which coal can be hydrogenated to produce oil and gas. In the processes of these patents, reactions between coal and hydrogen were carried out in the presence or absence of catalysts. At higher temperatures, catalysts were found to have relatively small effect. Gases resulting from these reactions were largely hydrocarbons mixed with the hydrogen gas used to hydrogenate the coal. Generally the hydrocarbon gases were in a range from 5 to approximately 35 volume percent of the gaseous products. My U.S. Pat. No. 3,762,773, issued Oct. 2, 1973, discloses a method and apparatus for feeding finely divided solids such as coal, to a pressurized gas or gas-liquid-solid system without loss of gas pressure from the pressurized system.

It is an object of the present invention to modify the prior hydrogenation procedures in such a way as to provide a highly efficient process for the conversion of coal into hydrocarbon oil and pipeline quality gas.

It is another object of the invention to make possible the conversion of a large portion, e.g. 80 percent or more, of the coal fed to hydrogenation to products consisting of oil and high Btu gases, particularly gases suitable for use in the replacement of natural gas in pipeline transmission and distribution systems.

This invention accomplishes these objects by use of a closed cyclic system in which a relatively large volume of hydrogen is circulated with coal, oxygen and steam being fed to one part of the cycle, and oil and high Btu gas being removed from another part. The coal is fed from pressurized feeders, preferably such as disclosed in my aforesaid U.S. Pat. No. 3,762,773, using recycle hydrogen from the system as the pressurizing gas. Hydrogen for the hydrogenation step is generated within the closed system at system pressure by feeding coal, oxygen and steam all at system pressure to a suitable gasification unit, thereby eliminating the need for a mechanical compression step to compress the hydrogen. Heat for the hydrogenation is also supplied by the gases generated in the gasifier. Oil is removed from the closed cyclic system as a liquid product by cooling and condensing. Cooled gases which are still at system pressure are washed with water or other suitable liquid to remove $H_2S$ and $CO_2$. The remaining gases are primarily hydrogen and hydrocarbons. These are separated into hydrogen gas and hydrocarbon gases by oil extraction or by cooling and liquifying the hydrocarbon gases. This separation is carried out at system pressure. The hydrogen remaining from the separation step is recycled to the hydrogenation reactor. The separated hydrocarbon gases, which are primarily methane, constitute the high-Btu gaseous product from the process. It is desirable to maintain a relatively large volume of recycle hydrogen in the system to provide the necessary equilibrum conditions for the hydrogenation reaction and to act as a carrier for the coal. Preferably the volume of hydrogen-containing recycle gas is at least three times the volume of the hot hydrogen-containing gases from the coal gasifier and the recycle gases contain at least 75% hydrogen and may contain above 90% hydrogen.

This hydrogenation process is related to the processes set forth in my aforementioned applications Ser. Nos. 268,201, filed June 30, 1972 and 412,026, filed Nov. 1, 1973 in that it employs a closed cyclic system. It differs from the processes disclosed in these applications in two major respects. First, the hydrogenation of the coal and of the tar is carried out under conditions providing a higher yield of hydrocarbon gas; second, this gas is separated from the hydrogen for use as pipeline gas before the hydrogen is recycled to be used for the process.

This invention is illustrated by the accompanying drawings, wherein:

FIG. 1. A and 1B together represent a flow diagram of a coal hydrogenation system embodying the principles of the invention.

Figure 1B:
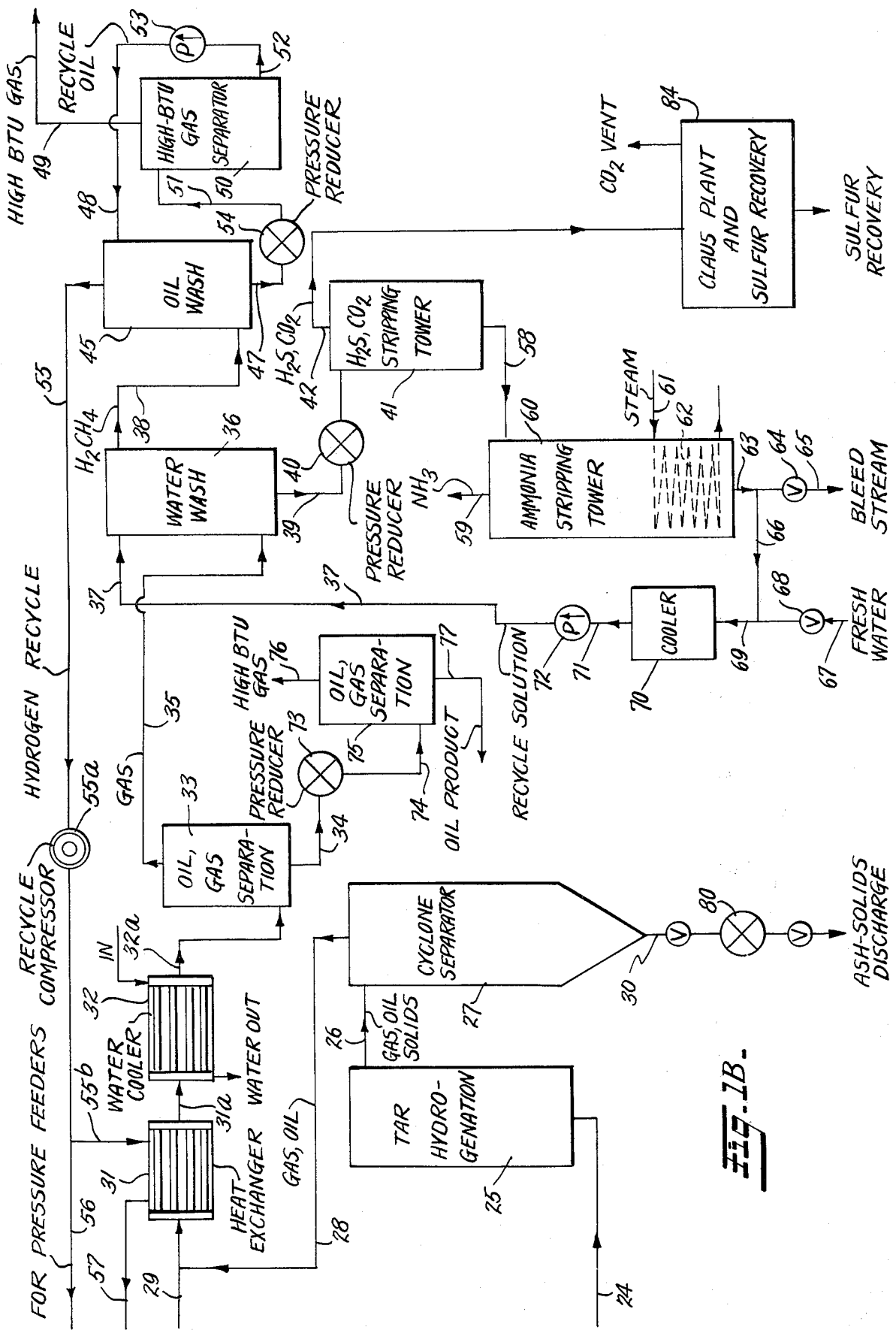
Figure 1C:
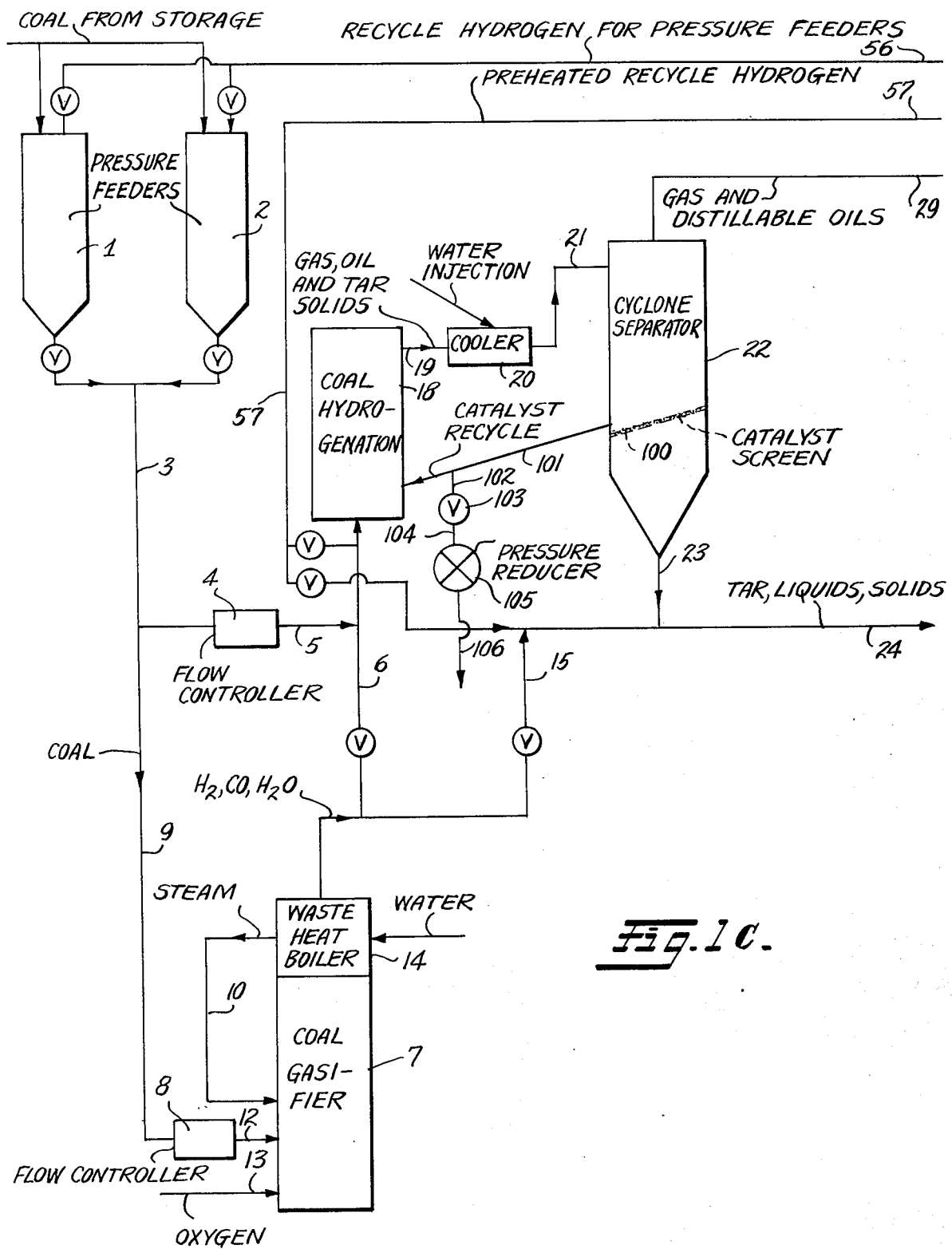

FIG. 1C is a flow diagram of a modified form of that portion of the system shown in FIG. 1A.

Referring to the flow diagram of FIGS. 1A and 1B, solid pulverized coal from a pressurized feeder vessel 1 or 2 is fed through line 3, line 5, and flow controller 4 into line 6. Preheated recycled hydrogen gas from the process flows through line 57 and joins the stream of coal in line 6. Recycled hydrogen gas which has not been preheated may be used to pressurize the coal feeders 1 and 2 through line 56 as shown.

Fresh hydrogen in sufficient quantity to supply all of the hydrogen requirements for the process is produced in coal gasifier 7. One means of producing the hydrogen in gasifier 7 is as follows: coal from the pressurized feeding units 1 or 2 flows through line 9 to flow controller 8 and then through line 12 to coal gasifier 7, which is operated at the pressure of the closed cyclic system. The pressure in the system is generally within the range of from about 1000 to 5000 psi, with the pressure in the hydrogen recycle lines 56 and 57 being slightly higher than that in the gasification and hydrogenation units in order to ensure flow through the system. Steam at the required pressure is generated from waste heat from the gasification operation and is fed to the gasifier through line 10. Oxygen generated at systems pressure in an air separation plant (not shown) is fed to the gasifier through line 13. It is desirable to preheat this oxygen to about 1000°F before it is fed to the gasifier.

The gasifier is preferably a refractory lined high pressure steel vessel equipped with a jacket for water cooling. Reactions in the gasifier between coal, oxygen and steam generate largely hydrogen and carbon monoxide, along with a small amount of carbon dioxide. It is desirable to run the gasifier at high temperatures since this increases the speed of the reactions and especially the rate of steam decomposition. It also reduces the amount of carbon dioxide in the gas. Operating temperature in the gasifier should not be below 2000°F and may be as high as 3000°F.

Primary control of the gasification temperature is by the amount of oxygen admitted, with more oxygen increasing the temperature.

The hot gases from the gasifier pass through waste heat boiler 14 to generate steam. The steam generated in the water cooled jacket of the gasifier and in the waste heat boiler may be used to supply steam to the gasifier.

The hot gases leaving the waste heat boiler section of the gasifier, which will generally be at a temperature of 1400°F or higher, leave through line 17 and mix with preheated recycled hydrogen in line 6. As heretofore noted, coal from the pressurized feeder also enters line 6 and the gases and coal flow to the first hydrogenation reactor 18. At the temperatures and pressures involved, the coal structure disintegrates and the hydrogen present and produced in situ reacts with the resulting fragments to produce smaller molecules which are hydrocarbon liquids and gases.

The temperature of the preheated recycled hydrogen and the temperature of the gases from the gasifier determine the temperature in coal hydrogenation reactor 18. The temperature of these gases must be high enough to heat the coal and gases in reactor 18 to reaction temperature, as well as to provide heat for the endothermic reaction:

$$C + H_2O \rightarrow CO + H_2$$

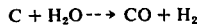

The hydrogenation of the coal to form oils is generally slightly exothermic. Hydrogenation of coal to methane is fairly strongly exothermic. In general, however, the gases coming through line 6 must be several hundred °F higher in temperature than the temperature in reactor 18.

The temperature in reactor 18 is primarily controlled by the temperature of the gases in line 17. In turn this temperature is controlled by the amount the gases are cooled in the waste heat boiler. One skilled in the art will have no difficulty in making the proper adjustments in these conditions.

During the reactions of coal and hydrogen in vessel 18 to form oils and hydrocarbon gases other materials, such as $H_2S$ and $NH_3$, are also formed. Neither $H_2S$ nor $NH_3$ interfere with the coal hydrogenation reactions even if they are carried out in the presence of a catalyst, since hydrogenation catalysts are normally resistant to poisoning by these compounds.

Retention time in vessel 18 will depend on the temperature and pressure in this vessel. My U.S. Pat. Nos. 3,030,297 and 3,152,063 have shown that dry coal hydrogenation to liquids and gas is very rapid and at suitable hydrogenation temperatures about 70 to above 90 percent of the coal can be converted to liquids and gas in less than a minute. The coal in vessel 18 may be maintained as a fluidized bed, but it is also possible to select conditions at which hydrogenation is fast enough to allow the coal to be entrained in the gas stream and still secure high conversion of the coal to oil and gas.

Major factors controlling the distribution between liquid and gas formation in the coal hydrogenation reactions in vessel 18 are:

1. temperature
2. pressure
3. reaction time

Coal may be hydrogenated at temperatures from about 600° to 1500°F or higher. At temperatures below about 800°F the reactions are slow and the degree to which the coal is hydrogenated is low. At temperatures from 800° to 1000°F coal particles suspended in hydrogen hydrogenate very rapidly and the amount of liquid formed may be above 70 percent of the coal hydrogenated. Pressures required for the hydrogenation are in the range from about 1000 to above 5000 psi. In the 800° to 1000°F temperature range the effect of the hydrogenation catalyst is important and suitable catalysts are required to give good liquid yields.

At increased temperature, liquid formation decreases and gas formation increases. For example, at 1100°F and about 15–25 seconds retention time at 2000 psi, gas production is about 80 percent and liquid production is about 20 percent of the coal converted. Under these conditions, increased pressure favors higher gas production. However, lower retention time favors increased liquid formation. Also, at temperatures above about 1050°F, the hydrogenation catalysts become much less important.

Gases, liquids, ash and unreacted coal leave reactor 18 through line 19. In vessel 20 the materials are cooled slightly, preferably by introduction of a small amount of water as a spray to condense the heavy oils and tars. From vessel 20 the gases, liquids and solids flow through line 21 to cyclone separator 22. Liquids and solids are separated from the gases in 22 and are removed through line 23. Alternate methods of separation may be used if desired. These materials are again hydrogenated in vessel 25 with hydrogen-containing gases brought in through line 24. The hydrogen-containing gases in line 24 are a combination of gases from gasifier 7 which enter at a controlled rate through line 15 and hot recycle hydrogen which enters at a controlled rate through line 16. The proportions of these gases may be adjusted to provide effective tar hydrogenation.

It has been noted that at temperatures below 1000°F, hydrogenation catalysts are required in reactor 18 to give good yields of gases and liquids. The catalyst may be sprayed on the coal in a liquid solution, it may be present as an ebullating or fixed bed, or it may be entrained in the gas stream. The manner in which the catalyst is used in a fixed or ebullating bed, and by spraying the catalyst on the coal, are well known in coal hydrogenation and need not be described here.

In dry coal hydrogenation the catalyst may be entrained in the hydrogen gas stream with the coal and furthermore may be separated from the gas stream in the pressure system and recycled to hydrogenate additional coal. A representative method by which this may be done is illustrated in FIG. 1C.

Coal ground to 80 percent minus 200 mesh is entrained in a rising hydrogen stream in reactor 18. An aggregate carrying the catalyst, sized to plus 100 mesh but sufficiently light to be entrained in the hydrogen stream, is mixed with the coal before it is introduced into the pressurized feeders. The aggregate may be coated or impregnated with a suitable concentration of catalyst, e.g. molybdenum salts or the like, to promote the hydrogenation reactions during passage through reactor 18.

Gases, liquids and solids, including the aggregate containing the catalyst, leave the reactor 18 through line 19, flow through cooler 20, and pass into the cyclone separator 22 through line 21 as heretofore noted. As shown in FIG. 1C, the cyclone separator in this embodiment is equipped with a catalyst screen 100 which has 100 mesh openings. Unreacted coal and ash particles which are now less than 200 mesh will pass through this screen along with the tar and heavy liquids to the bottom of the cyclone separator and flow out through line 23 to the tar hydrogenator 25. Catalyst accumulated on catalyst screen 100 is returned through line 101 to hydrogenation vessel 18.

In this cycle the catalyst will become mixed with some ash and in time will deteriorate due to the presence of tar and carbon on the surface. A portion of the catalyst may be withdrawn through line 102, valve 103, line 104, pressure reduction 105 and line 106 to an apparatus (not shown) for treatment to restore its activity. The regenerated catalyst may then be mixed with the coal supplied to the pressure feeders.

It will be understood that after the system has attained normal operating conditions after start-up, catalyst will be added to the coal only as may be necessary to make up for catalyst losses.

Referring again to FIGS. 1A and 1B, hydrogenation conditions in the tar hydrogenator 25 determine the relative amounts of liquid or gaseous hydrocarbon products produced from the tar. The gas pressure in this vessel may remain at the selected system pressure, e.g. approximately 2000 psi. Temperatures may be in the 600° to 1000°F range. Liquid production is favored by slightly lower temperatures, smaller amounts of less active catalysts, and slightly longer retention times.

As an example, operating conditions in the tar hydrogenation to produce 70 to 90 percent yield of liquid products are: 900°F, retention time of approximately 30 to 60 seconds, and a catalyst concentration of about 0.5 percent of ammonium molybdate based on the weight of the tar. This amount of catalyst, if not already present due to carry over from the coal hydrogenation in the presence of catalyst, may be added under pressure to line 24 by any suitable means and may be recovered from the residual solids.

Products from vessel 25 pass through line 26 to cyclone separator 27 where the ash and remaining solids are separated. Overhead material from separator 27 passes through line 28 and joins the material coming from separator 22 through line 29.

Ash and any residual tar and solids are removed at the bottom of separator 27 through line 30 using any suitable pressure reduction device 80.

In the method of operation which has been described, hydrocarbon gas, distillable hydrocarbon oils, and tars are produced in both coal hydrogenation vessel 18 and tar hydrogenator 25. An alternate method of operation which is especially suitable for reactive coals such as low rank bituminous, subbituminous or lignitic may also be used as follows:

Hydrogenation in vessel 18 is carried out with coal and catalyst entrained in the gas stream using a retention time of about 20 seconds at about 900°F. This will convert approximately 50 percent of the coal to a distillable liquid and the rest to tar and hydrocarbon gas. In vessel 22 the distillable oils and gas are separated from the tar and solids. These latter materials are then hydrogenated over a fixed bed catalyst, such as a bed of cobalt-molybdenum on alumina, in tar hydrogenator 25 at about 950°F with a retention time of about 20 to 30 seconds to convert the tar to essentially all gas. This gas is separated from the remaining solids in cyclone separator 27. This method of operation produces essentially dry solids which are then discharged through line 30 and the pressure reduction system indicated.

It will be understood that suitable conditions can be selected in the coal and tar hydrogenation zones to produce mixtures of hydrocarbon liquids and gases in substantially any desired proportions.

The liquid and gas products which flow from lines 28 and 29 are cooled in heat exchanger 31 and flow through line 31a for further cooling in water cooler 32 to condense oil vapors to liquid. Gas and oil from cooler 32 flow through line 32a to oil-gas separator 33. From separator 33 the oil is withdrawn through line 34 and the pressure on the liquid is reduced to atmospheric in pressure reduction 73. The oil then flows through line 74 to oil-gas separator 75. In this vessel the dissolved gases in the oil, which are mainly methane and higher hydrocarbon gas, will separate from the oil at the reduced pressure. These gases are withdrawn through line 76 and since they have a high Btu value they may be added directly to the product gases from the process.

Oil is withdrawn from vessel 75 through line 77 and this is the oil product of the process. This is a completely distillable oil which will have a sulfur content below 0.5 percent and is suitable for refining by known petroleum processing steps.

The gas separated from the oil in separator 33 is a mixture of hydrogen and hydrocarbon gases. It flows through line 35 to water wash vessel 36. Water enters the top of water wash 36 through line 37. Gas from line 35 flows counter current to the flow of liquid. The purified gases, which are largely $H_2$, methane and higher hydrocarbon gases, leave through line 38.

The wash solution containing $CO_2$, $H_2S$, and ammonia, leaves through line 39. The pressure is reduced in pressure reduction device 40 and the solution flows into stripping tower 41. At low pressures the $H_2S$ and $CO_2$ are separated from the solution and leave through line 42. The solution which still contains ammonia leaves the bottom of tower 41 through line 58 and enters ammonia stripping tower 60, where the ammonia is largely removed by heating the solution. Heat is provided by steam entering through line 61 into heating coil 62. The ammonia leaving through line 59 may be recovered by compression to liquid ammonia or may be dissolved in water to make an ammonia solution.

The wash solution leaves tower 60 through line 63 and line 66 and flows through line 69 to cooler 70. Valves and lines are provided at 64 and 65 to bleed the solution from the system to prevent the accumulation of excessively high concentrations of undesirable materials in the solution. Also, if desired, fresh water may be admitted through line 67 and valve 68.

The cooled recycled solution from 70 leaves through line 71, is brought back to systems pressure in pump 72, and then recycled through line 37 to water wash 36.

Preferably the $H_2S$ and $CO_2$ leaving the top of stripping tower 41 are not vented to the atmosphere. These gases may be taken to an apparatus such as a Claus plant 84 to convert the $H_2S$ to sulfur. The sulfur can be recovered as liquid or solid sulfur.

The hydrogen and hydrocarbon gases leave water wash 36 through line 38. Depending on the conditions of operation, these gases may contain from about 15 to over 50 volume percent methane and higher hydrocarbons.

The hydrocarbon gas may be separated from the hydrogen in any suitable manner such as by washing the gases under pressure with a suitable fraction of gas oil from the process or by using a cryogenic process to cool the hydrocarbon gases to the point of liquification while the hydrogen remains in the gaseous phase. Since hydrogen remains as a gas at very low temperatures this method provides an effective separation of hydrocarbon gases from hydrogen.

At pressures of approximately 2000 psi and 70°F the solubility of methane in a mixed aromatic-paraffinic oil, boiling in the range from 280° to 350°F, is about 9 times the solubility of hydrogen gas on a volume basis. Under lower or atmospheric pressures the solubility of the methane in the oil is much less.

This change in methane solubility with pressure can be used to separate the hydrocarbon gases from hydrogen. Referring to FIGS. 1A and 1B, it will be seen that the mixed gases in line 38 enter the bottom of oil wash tower 45. The gases flow up the wash tower 45 and the wash oil, which comes into the top of the tower 45 through line 48, flows down the tower 45. The oil absorbs the hydrocarbon gases and leaves the oil wash tower 45 through line 47. After passing through pressure reduction 54, the oil passes through line 51 and enters high Btu gas separation tower 50 which operates at about 100–500 psi. The reduction in pressure permits the gas to separate from the oil and the hydrocarbon gases may be removed through line 49. These hydrocarbon gases are the gaseous products from the process and are mainly methane containing small amounts of higher hydrocarbons and approximately 10 percent of hydrogen.

The oil leaving the high Btu gas separation tower 50 through line 52 is restored to system pressure by pump 53 and is then returned through line 48 to the oil wash tower.

The solubility of hydrogen in the oil used in washing is low and therefore most of the hydrogen is available for recycling to the process. The gas from which the hydrocarbon products have been removed contains over 75 percent hydrogen and may contain over 95 percent hydrogen depending on the solvent and conditions used. This gas passes from oil wash tower 45 through line 55 to recycle compressor 55a. The recycle compression 55a restores the pressure drop that has occurred during the passage of the gas through hydrogenation, oil separation, gas purification, and methane separation. It is preferable to compress the recycle hydrogen to a pressure slightly above the system pressure so as to ensure flow of materials through the closed cycle of operations. Line 55b carries the recycle gas to heat exchanger 31 where it is heated by the outgoing gases from hydrogenation. The gas is then returned through line 57 to line 6 and then to coal hydrogenation vessel 18 for recycling through the processes.

Solvents other than hydrocarbon oils may also be used to separate the hydrocarbon gases from hydrogen. Solvents, such as lower aliphatic alcohols or ethers, can be used and will operate effectively at the lower pressure range of the system.

It has also been noted that an alternate cryogenic process may be used to separate the hydrocarbon gases from the hydrogen gas which is to be recycled. In this process ( which is not shown ) the mixed gases under pressure in line 38 are cooled through heat exchangers to a suitable temperature to liquify the hydrocarbon gases and to leave the hydrogen in the gaseous state. The hydrocarbon gases are withdrawn from the system while they are in the liquid state and are thereby separated from the hydrogen. Since the temperature of liquification for methane is about 160°F higher than that for hydrogen, this separation is highly effective. The cold gases leaving the liquification process are then heat exchanged with incoming gases so that the process has reasonably high thermal efficiency. The gaseous hydrogen recovered from this process may be recycled back through a recycle compressor, as shown in FIG. 1B.

EXAMPLE

Coal supplied to the process in FIGS. 1A and 1B normally contains hydrogen in amounts ranging from about 4 to 6 percent. Oil produced from the hydrogenation process contains from 11 to 14 percent hydrogen and the gaseous hydrocarbon products will contain up to 25 percent by weight of hydrogen (for methane). Hydrogen is also needed to convert the sulfur in the coal to $H_2S$ and the nitrogen to $NH_3$. Part of the oxygen in the coal is converted to $H_2O$ and part to $CO_2$. Therefore, to convert coal to liquid and gaseous products there is needed an addition of hydrogen to the coal in amounts ranging from about 6 to 11 percent.

This hydrogen is supplied by the hydrogen generation step shown in FIG. 1A, which has been described.

The following will illustrate the application of the process for the conversion of bituminous coal to liquid and gaseous hydrocarbons. The ultimate analysis of the coal in this case on a moisture and ash free basis ( maf ) is as follows:

| Component | Weight percent |
|---|---|
| C | 83.0 |
| $H_2$ | 6.0 |
| $O_2$ | 4.2 |
| $N_2$ | 3.5 |
| S | 3.3 |
| TOTAL | 100.0 |

The heating value on the maf basis is 15,200 Btu per lb.

Conversion of the carbon in the coal on a weight basis to one-half methane and one-half liquid hydrocarbons requires the addition of approximately 15 lbs. of hydrogen to 100 lbs. of maf coal.

The operating conditions in the coal hydrogenation reactor for this conversion are approximately as follows:

| | |
|---|---|
| Pressure | 2000 psi |
| Temperature | 1000°F |
| Coal feed rate (maf) | 5 tons per minute |
| Coal entrained in circulating gas Retention time | 20 seconds |
| Hydrogen recycle rate | 1100 thousand standard cubic feet per minute (To reactors 18 and 25) |
| Gas feed from coal gasifier (basis dry gas) | 277 thousand standard cubic feet per minute |

In addition to the coal fed to the hydrogenation reactor, approximately 4.7 tons per minute will be needed for gasification and about 1 ton per minute for steam and power. The total coal requirements are 10.7 tons per minute or about 15,400 tons per 24 hours.

Daily output from the plant is as follows:
Distillable oils    23,700 barrels
High Btu gas    180 million standard cubic feet The thermal efficiency of the plant on the basis of the heating value of the liquid and gaseous products divided by the heat in the total coal fed to the plant is between 65 and 70 percent. The liquid products are distillable oils containing less than 0.5 percent sulfur on a weight basis. The high Btu gas is essentially free from sulfur.

The conditions set forth in the foregoing example are illustrative of one representative process. It is to be understood that these conditions may be varied in many ways. It is not intended that the application of the various steps and conditions described be limited only to the representative example set forth.

I claim:

1. A process for hydrogenating coal to provide hydrocarbon oil and gas products, comprising: hydrogenating said coal in the substantial absence of externally supplied liquid slurrying medium in a hydrogenation zone of a closed cyclic system, said system being maintained under hydrogenation pressure, with hot recycled hydrogen-containing gases and with added hot hydrogen-containing gases generated by reaction of coal at system pressure with oxygen and steam to provide an effluent stream containing excess hydrogen and liquid and gaseous hydrocarbons, removing liquid hydrocarbon products from said effluent stream without substantial reduction in system pressure, purifying the resulting effluent gas stream to remove $H_2S$, $CO_2$ and $NH_3$ without substantial reduction in system pressure, separating hydrocarbon gases from the hydrogen of the purified gas stream without substantial reduction in the hydrogen pressure to provide a gaseous hydrocarbon product of high Btu content, and recycling the resultant hydrogen stream through the closed system to said hydrogenation zone.

2. The process of claim 1 in which the pressure in the closed cyclic system is between about 1000 to 5000 psi, the temperature in the hydrogenation zone is maintained in the range of about 600° to 1500°F, the volume of recycle hydrogen is at least three times the volume of the added hot hydrogen-containing gases and the hydrogen concentration of the recycle hydrogen gases is above 75 percent hydrogen.

3. The process of claim 2 wherein hydrogenation of the coal is carried out in the presence of a hydrogenation catalyst.

4. The process of claim 2 wherein the temperature in the hydrogenation zone is maintained in the range of about 800°F to 1000°F to produce primarily liquid hydrocarbon products from the coal.

5. The process of claim 1 in which the added hot hydrogen-containing gases are produced at a temperature in excess of hydrogenation temperature to thereby provide heat for use in the hydrogenation zone.

6. The process of claim 1 wherein the product stream from the hydrogenation zone is cooled by indirect heat exchange to condense tars and solids, the tars and solids are introduced at system pressure into a tar reactor along with recycled hydrogen containing gases and added hot hydrogen-containing gases, the tars are hydrogenated to provide a hydrocarbon containing product stream, solids are removed from the product stream from the tar reactor without pressure reduction on this stream and the resulting product stream from the tar reactor is combined with the main product stream.

7. The process of claim 1 wherein the stream of gases after removal of liquid hydrocarbons is purified by contact with water at system pressure to remove $H_2S$ and $CO_2$ prior to separation of the gaseous hydrocarbons from the hydrogen.

8. The process of claim 1 wherein coal is added to the system through feeders pressurized by a portion of the continuously circulating hydrogen containing gases in the closed cyclic system.

9. The process of claim 1 wherein the gaseous hydrocarbons are separated from the hydrogen by contacting the gas stream with a solvent in which the gaseous hydrocarbons are preferentially soluble at the system pressures.

10. The process of claim 9 in which said solvent is a mixed aromatic-paraffinic oil.

11. The process of claim 1 wherein hydrogen is separated from the hydrocarbon gases by liquifying the hydrocarbon gases.

12. The process of claim 3 wherein the hydrogenation catalyst is introduced into the hydrogenation zone with the coal.

13. The process of claim 12 wherein said catalyst is supported on a particulate carrier of larger particle size than the particle size of the coal, the coal and catalyst are entrained in the gases entering the hydrogenation zone and the catalyst is screened from the effluent stream from the hydrogenation zone and recycled to hydrogenate additional coal.

14. A process for producing hydrocarbon oils and gases of high Btu content from coal comprising: continuously feeding coal in the substantial absence of externally supplied liquid slurrying medium under gas pressure into a closed pressurized system maintained under hydrogenation pressure and having a coal gasification zone and first and second hydrogenation zones, feeding part of the coal to the coal gasification zone and reacting it with oxygen and steam to produce hot hydrogen-containing gases, feeding another part of said coal to the first hydrogenation zone along with a portion of said hot hydrogen-containing gases, hydrogenating said coal in said first hydrogenation zone with said hydrogen-containing gases and with recycle hydrogen from the closed system to provide an effluent stream containing hydrogen, hydrocarbon oils and gases and residual tars and solids, separating said residual tars and solids from the effluent stream and hydrogenating them in said second hydrogenation zone with another portion of the hot hydrogen-containing gases from the coal gasified and with recycle hydrogen from the system to provide a second hydrocarbon-containing effluent stream, combining the two effluent streams and removing hydrocarbon oils from the combined stream without reducing the pressure on the system, purifying the resulting gaseous stream to remove $H_2S$, $CO_2$ and $NH_3$ without substantial pressure reduction, separating gaseous hydrocarbons from the hydrogen in said purified gaseous stream without substantial pressure reduction on the system and recycling the hydrogen to the hydrogenation zones of the closed system.

\* \* \* \* \*

UNITED STATES PATENT OFFICE
CERTIFICATE OF CORRECTION

Patent No. 3,944,480　　　　　　　　Dated　March 16, 1976

Inventor(s)　WILBURN C. SCHROEDER

It is certified that error appears in the above-identified patent and that said Letters Patent are hereby corrected as shown below:

Column 3, line 45,　　change "interfer" to --interferes--.

Column 7, line 1,　　change "liquification" to --liquefaction--.

Column 7, line 42,　　change "compression" to --compressor--.

Column 7, line 53,　　change "processes" to --process--.

Column 8, line 1,　　change "liquification" to --liquefaction--.

Column 8, line 3,　　change "liquification" to --liquefaction--.

Signed and Sealed this

Tenth Day of August 1976

[SEAL]

Attest:

RUTH C. MASON
Attesting Officer

C. MARSHALL DANN
Commissioner of Patents and Trademarks